United States Patent [19]

Velten

[11] Patent Number: 5,251,647
[45] Date of Patent: Oct. 12, 1993

[54] METHOD FOR INTRODUCING A TRANSPONDER TOGETHER WITH A DISINFECTANT

[75] Inventor: Henk Velten, Enter, Netherlands

[73] Assignee: Texas Instruments Incorporated, Dallas, Tex.

[21] Appl. No.: 775,667

[22] Filed: Oct. 11, 1991

[30] Foreign Application Priority Data

Oct. 11, 1990 [NL] Netherlands ............... 9002215

[51] Int. Cl.⁵ .................... A61B 19/00; A61B 5/07
[52] U.S. Cl. ........................ 128/899; 119/174; 128/655; 128/631
[58] Field of Search ............ 604/64; 424/426, 438; 119/51.02, 174; 128/631, 653.4, 655, 899; 606/117, 175

[56] References Cited

U.S. PATENT DOCUMENTS

| | | | |
|---|---|---|---|
| 4,876,093 | 10/1989 | Theeuwes et al. | 424/438 |
| 4,961,698 | 10/1990 | Vlock | 433/119 X |
| 5,074,318 | 12/1991 | Campbell et al. | 128/899 |
| 5,135,523 | 8/1992 | Magruder et al. | 424/438 X |

FOREIGN PATENT DOCUMENTS

| | | |
|---|---|---|
| 0049068 | 4/1982 | European Pat. Off. . |
| 0255123 | 2/1988 | European Pat. Off. . |
| 0292936 | 11/1988 | European Pat. Off. . |
| 8901858 | 2/1991 | Netherlands ............... 128/631 |
| 8902283 | 2/1991 | Netherlands . |

Primary Examiner—Robert P. Swiatek
Attorney, Agent, or Firm—Rebecca A. Mapstone; James C. Kesterson; Richard L. Donaldson

[57] ABSTRACT

Method for identifying an animal wherein a transponder is (3) introduced in the animal. To prevent infection of the wound site, together with the transponder (3) a disinfectant is introduced. According to the invention, this disinfectant is present in a bioabsorbable tablet (14) and this tablet (4) is introduced in line with the transponder.

8 Claims, 1 Drawing Sheet

METHOD FOR INTRODUCING A TRANSPONDER TOGETHER WITH A DISINFECTANT

The invention relates to a method for introducing a transponder into a living being together with a disinfectant.

BACKGROUND OF THE INVENTION

In the prior art it is generally known to fit transponders in living creatures for identification purposes. A transponder of this type usually comprises a housing inside which electronic components are installed. These electronic components comprise a transmitter unit, receiving unit and a memory storage unit. By irradiating the transponder with a beam from an outside source, the transmitter is activated to transmit the data stored in the memory. In this way it is possible to identify animals. In the abovementioned PCT application, an application of this type is described for fish. In this case, the transponder is introduced into the living creature with the aid of an injection needle. With the aid of the injection needle, an opening is first made in the skin of the living creature. The injection needle then serves as a guide through which the transponder is moved. Transport of the transponder through the injection needle can be carried out using mechanical means. It is also possible to allow this transport to take place by means of fluid means. That is to say, an amount of fluid is located behind the transponder. By applying pressure in the cylinder of the injection syringe, this pressure is transmitted to the fluid and moves the transponder into the body of the animal concerned. When transponders are introduced into living creatures there is always the problem of infection of the wound. This is in the main caused by the fact that contaminants which are present on the skin are brought into the body during the injection. If a circular cut is made in the skin, this circular section of skin in front of the transponder is moved into the body of the living creature. As a result of this inflammation can occur, with all the associated undesired rejection reactions. This can result in the transponder being driven out of the body. In order to prevent this, it is proposed that the fluid be allowed to contain disinfectants. In practice, however, it has been found that it cannot be guaranteed that a controlled amount of disinfectant is present in the vicinity of the transponder immediately after introduction. At the same time there is also the problem that infections show themselves only after a prolonged period. The fluid introduced with the transponder will be absorbed relatively rapidly from the site of introduction into the body, as a result of which disinfectant is no longer present at a later time, while it is still needed at this location.

The aim of the present invention is to overcome this disadvantage.

SUMMARY OF THE INVENTION

This aim is achieved in the case of a method described above by incorporating the disinfectant in a bioabsorbable tablet to be introduced with the transponder, it is ensured that an adequate amount of disinfectant is present in the body of the living creature concerned, while by means of an appropriate choice of the rate of release of the disinfectant, infection can also be prevented in the longer term.

DETAILED DESCRIPTION OF THE PREFERRED EMBODIMENTS

In one case of the device, the fluid is necessarily introduced behind the transponder into the living creature. After all, the fluid is the driving medium for introducing the transponder into the living creature. At the same time, the transponder provides a closure for the fluid present in the cylinder of the syringe. As already indicated above, it has, however, been found that, in particular, infection occurs as a result of contamination which originates from the skin and moves with or in front of the transponder into the interior of the animal. As a result of this, inflammation will occur in the vicinity of or in front of the transponder. Inflammation of this type is more harmful than inflammation behind the transponder, that is to say inflammation closer to the skin. After all, the body of living creatures strives to work contaminants and other undesired articles to the outside by means of the tissue becoming softer in the vicinity of the undesired article and an outwardly directed movement. If contamination is present behind the transponder, that is to say closer to the skin, this contamination will move to the outside without this influencing the position of the transponder. If, however, contamination is present in the vicinity of or in front of the transponder, that is to say deeper in the body, there will be a risk that as this contamination is moved outwards the transponder will also be moved outwards with it. In practice, it has been found that the transponder can easily be lost in this way, with all the associated adverse consequences. In order to overcome this disadvantage, it is proposed, in accordance with an advantageous embodiment of the invention, to introduce the agents in front of the transponder. That is to say that if, for example, the transponder is introduced with the aid of an injection needle, which may or may not be closed, the disinfectant is introduced in front of the transponder. This introduction of the disinfectant together with the transponder can be achieved by all of the methods known in the prior art, that is to say with the aid of mechanical means or with the aid of fluid pressure. Since the disinfectant is now located in front of the transponder, that part of the living creature which is most critical with regard to inflammation will be directly provided with a disinfectant, by which means inflammation in front of and in the vicinity of the transponder is prevented and it is thus possible, in a guaranteed manner, to prevent the transponder leaving the body as a result of a defence reaction.

According to an advantageous embodiment of the invention, a circular cut is not made in the skin of the animal, as is the case in accordance with the prior art. After all, when a closed circular cut is made, the section of skin thus released will move inwards and the contamination present on the section of skin will constitute a source of defence reactions by the body of the living creature. According to the invention it is proposed to make a U-shaped cut, followed by folding back of the section of skin thus formed, and the introduction of the transponder and the disinfectant. The section of skin can then be moved back into its original position. With this method the only risk which still exists is that dirt adhering to the section of skin which is moved inwards with the transponder, but this contamination is much less serious than contamination of the entire section of skin itself in connection with the rejection reaction to be anticipated by the body and is prevented by the measures according to the invention.

The invention also relates to a disinfectant for introduction in front of a transponder into a living creature, said disinfectant comprising a bioabsorbable tablet essentially having the same cross-sectional shape as the transponder. In this way it is possible with the aid of, for example, an injection needle, to introduce both the transponder and the disinfectant. The use of ointments or liquids, comprising disinfectant, on the transponder will always result in a high concentration of such compounds behind the transponder (in the direction of introduction) a low concentration at the sides of the transponder and no disinfectant at all in front of it, whilst dirt will normally be found in front of the transponder. Use of a tablet according to the invention and introducing such a tablet in front of the transponder will obviate such an undesired concentration gradient. If the disinfectant and the transponder are introduced without an aid, such as an injection needle, the tablet, according to an advantageous embodiment of the invention, is shaped such that the end which first comes into contact with the skin of the living creature is tapered to a point and the tablet is joined to the transponder. By this means, a path can be made more easily for the disinfectant and the transponder.

The tablet preferably contains a carrier based on protein material with the disinfectant incorporated therein. This disinfectant can comprise any substance known in the prior art. The protein material preferably corresponds to the proteins which correspond to the proteins of the living creature concerned. By this means it is possible to prevent rejection reactions.

Other bioabsorbable agents which are preferred for the carrier comprise polylactic acid.

BRIEF DESCRIPTION OF THE DRAWINGS

The invention will be illustrated in more detail below with reference to an illustrative embodiment illustrated in the drawing. In said drawing.

Figure 1:
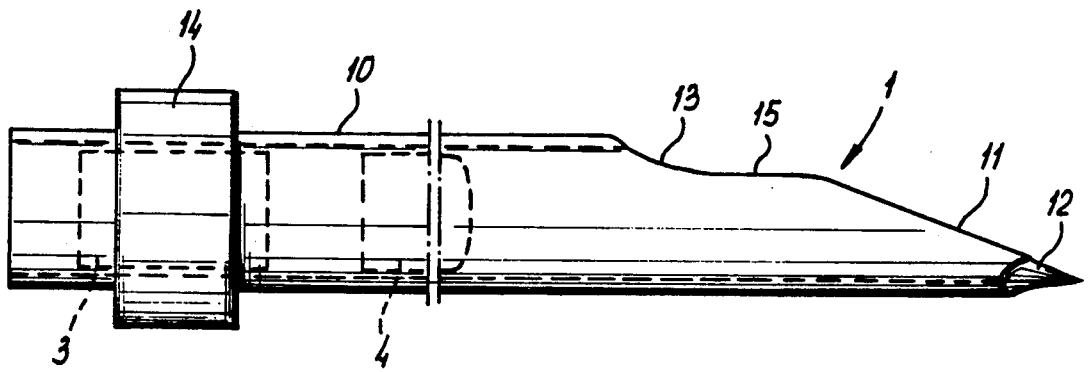
FIG. 1 shows, partially in cross-section, a side view of an insertion needle provided with a transponder and the disinfectant according to the invention
Figure 2:
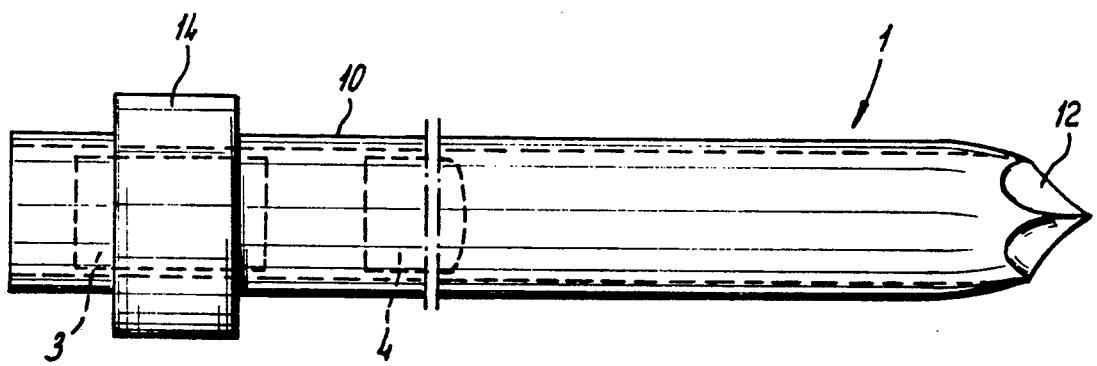
FIG. 2 shows a top view of the device according to FIG. 1.
Figure 3:
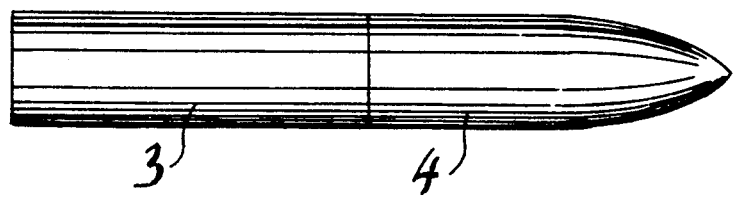
FIG. 3 shows a side view of a pointed bioabsorbable tablet joined to a transponder.

It can be seen from FIGS. 1 and 2 that a needle, indicated in its entirety by 1, is shaped so that it slopes at the front. This needle is provided with a sloping section 11, which on one side joins an end 12 provided with facets and on the other side is bounded by a horizontal section 15. A transitional section 13 is also present, which joins the end of the needle to the needle body 10. This needle body 10 is joined, in a manner not shown, to an insertion gun via a coupling 14. A transponder 3 and a tablet 4 containing disinfectant according to the invention are shown in the needle. Said tablet 4 consists of a carrier with a disinfectant incorporated therein.

The carrier can consist of polylactic acid or a substance based on a protein material compatible with the protein material of the living creature into which the transponder is fitted. The disinfectant can comprise any disinfectants known in the prior art. The transponder 3 is a transponder customary in the prior art. This can be, for example, a glass transponder in Which electronic components, consisting of a transmitter/receiver aerial, a memory and a transmitter and receiver, are incorporated. When the transponder is irradiated with a beam, said transponder emits a signal which contains data which correspond to the data stored in the memory.

The device described above functions as follows:

If it is desired for any reason to identify a living creature, it is desirable to fit a transponder 3 in said creature. To this end, a U-shaped cut is made in the skin by inserting needle This is described in more detail in Netherlands Patent Application 8902938, which has not previously been published. After inserting the needle in the body of the living creature, the transponder 3 is driven, with the aid of means which are not shown, into the body of the animal, the tablet 4 moving in front of said transponder. Both brush by the section of skin folded inwards, as a result of which there is a risk that, despite the pre-cleaning of the area concerned, further contaminants are carried into the body of the living creature concerned. Since the tablet 4 is introduced into the living creature in front of the transponder, infection is vigorously combated at said location by the release of disinfectant from the tablet 4. By this means the occurrence of inflammation at the "upstream site" of the transponder, which in particular is dangerous because it can result in a defence reaction which results in the transponder being driven out of the body, is prevented. If an insertion needle is not used, tablet 4 is preferably provided with a sharp point and joined to the transponder. By this means, a path can easily be made in the body of the living creature. The release of disinfectants can vary from hours to days. This is in contrast to agents which are used in the prior art, such as iodine, which is active for at most one hour.

In practice it has been found that the failure of transponders can be appreciably reduced by introducing the disinfectant in front of the transponder.

Although a preferred embodiment of the invention has been described above, it must be understood that numerous modifications may be made thereto. Thus, it is possible to integrate the front of the transponder and the disinfectant. It is also possible to incorporate the transponder in a hollow in a cylindrical carrier for disinfectant. These and all other modifications all lie within the scope of the present invention.

I claim:

1. A disinfectant/transponder assembly for introduction into a living creature, comprising a bioabsorbable tablet disinfectant essentially having the same cross-sectional shape as the transponder wherein aid bioabsorbable tablet is introduced into the living creature in front of said transponder.

2. A disinfectant/transponder assembly according to claim 1, wherein one end of said bioabsorbable tablet is joined to said transponder and said other end of said bioabsorbable tablet which first comes into contact with said living creature is pointed.

3. A method for providing identifying information relative to a particular living creature comprising the steps of:

introducing a transponder under the skin of said living creature together with a disinfectant, wherein said disinfectant is present in a bioabsorbable tablet and is introduced in line with said transponder.

4. A method according to claim 3, in which the disinfectant is introduced in front of the transponder.

5. A method according to claim 3, further comprising making a U-shaped cut in the skin of the living creatures, folding back the section of skin thus formed and inserting the transponder and the disinfectant.

6. A disinfectant/transponder assembly for introduction into a living creature wherein said disinfectant comprises a carrier material with a disinfectant incorporated therein, and said carrier material has essentially the same cross-sectional shape as said transponder.

7. A disinfectant/transponder assembly according to claim 6, in which the carrier for a disinfectant contains polylactic acid.

8. A disinfectant according to claim 6, in which the carrier consists of protein which corresponds to the proteins of the living creature into which the transponder is introduced.

* * * * *